US012761121B2

(12) United States Patent
Kajita et al.

(10) Patent No.: US 12,761,121 B2
(45) Date of Patent: Oct. 13, 2026

(54) SENSOR ELEMENT AND METHOD OF MANUFACTURING SENSOR ELEMENT

(71) Applicant: NGK INSULATORS, LTD., Nagoya (JP)

(72) Inventors: Yuki Kajita, Kasugai (JP); Yuma Tanabe, Komaki (JP)

(73) Assignee: NGK INSULATORS, LTD., Nagoya (JP)

( * ) Notice: Subject to any disclaimer, the term of this patent is extended or adjusted under 35 U.S.C. 154(b) by 282 days.

(21) Appl. No.: 18/604,553

(22) Filed: Mar. 14, 2024

(65) Prior Publication Data

US 2024/0328907 A1 Oct. 3, 2024

(30) Foreign Application Priority Data

Mar. 30, 2023 (JP) ................................ 2023-054709

(51) Int. Cl.

| | |
|---|---|
| ***G01N 1/22*** | (2006.01) |
| ***C23C 4/02*** | (2006.01) |
| ***C23C 4/134*** | (2016.01) |
| ***G01N 27/407*** | (2006.01) |
| ***G01N 33/00*** | (2006.01) |
| *C23C 24/04* | (2006.01) |

(52) U.S. Cl.
CPC ......... *G01N 1/2205* (2013.01); *G01N 1/2252* (2013.01); *G01N 27/4077* (2013.01); *G01N 33/0037* (2013.01)

(58) Field of Classification Search
CPC ............... G01N 1/2205; G01N 1/2252; G01N 27/4077; G01N 33/0037; G01N 33/0009; C23C 4/02; C23C 4/134; C23C 24/04
See application file for complete search history.

(56) References Cited

U.S. PATENT DOCUMENTS

| | | | | |
|---|---|---|---|---|
| 2008/0156644 A1 | 7/2008 | Suzuki et al. | | |
| 2009/0188620 A1 | 7/2009 | Okuda et al. | | |
| 2016/0161445 A1 | 6/2016 | Sakakibara et al. | | |
| 2020/0182182 A1 | 6/2020 | Imada et al. | | |
| 2021/0199617 A1* | 7/2021 | Onishi | ............... | G01N 27/4071 |
| 2021/0356423 A1* | 11/2021 | Mori | .................. | G01N 27/4077 |

FOREIGN PATENT DOCUMENTS

| | | |
|---|---|---|
| JP | 2008-164411 A | 7/2008 |
| JP | 2009-80111 A | 4/2009 |
| JP | 2009-175099 A | 8/2009 |
| JP | 2016-109685 A | 6/2016 |
| JP | 2019-039693 A | 3/2019 |

* cited by examiner

*Primary Examiner* — Laura Martin Sweeney
*Assistant Examiner* — Anthony W Megna Fuentes
(74) *Attorney, Agent, or Firm* — MATTINGLY & MALUR, PC

(57) ABSTRACT

A sensor element is equipped with a main body including a cavity for taking in a gas on a distal end side thereof, and a porous protective layer covering an outer peripheral surface of the main body at the distal end side thereof. The porous protective layer is equipped with a water droplet blocking structure covering at least a part of a distal end surface, the part overlapping the cavity in a longitudinal direction, and a thin portion covering the distal end surface around the water droplet blocking structure.

11 Claims, 8 Drawing Sheets

FIG. 8

| | PRESENCE OR ABSENCE OF THIN PORTION ON EXTENSION LINE OF CAVITY IN LONGITUDINAL DIRECTION | THICKNESS A OF CONVEX PORTION [μm] | DIFFERENCE VALUE B IN THICKNESS BETWEEN THIN PORTION AND THE CONVEX PORTION [μm] | B/A | WATER RESISTANCE | PRODUCTIVITY |
|---|---|---|---|---|---|---|
| COMPARATIVE EXAMPLE1 | ABSENCE | 500 | – | – | ○ | △ |
| COMPARATIVE EXAMPLE2 | PRESENCE | 530 | 130 | 0.25 | × | ○ |
| COMPARATIVE EXAMPLE3 | PRESENCE | 500 | 320 | 0.64 | × | ◎ |
| EXEMPLARY EMBODIMENT1 | ABSENCE | 500 | 50 | 0.1 | ○ | ○ |
| EXEMPLARY EMBODIMENT2 | ABSENCE | 480 | 280 | 0.58 | ○ | ◎ |
| EXEMPLARY EMBODIMENT3 | ABSENCE | 900 | 300 | 0.33 | ◎ | ○ |
| EXEMPLARY EMBODIMENT4 | ABSENCE | 500 | 300 | 0.6 | △ | ◎ |
| EXEMPLARY EMBODIMENT5 | ABSENCE | 600 | 30 | 0.05 | ○ | △ |

SENSOR ELEMENT AND METHOD OF MANUFACTURING SENSOR ELEMENT

CROSS-REFERENCE TO RELATED APPLICATIONS

This application is based upon and claims the benefit of priority from Japanese Patent Application No. 2023-054709 filed on Mar. 30, 2023, the contents of which are incorporated herein by reference.

BACKGROUND OF THE INVENTION

Field of the Invention

The present invention relates to a sensor element for detecting gas components and a method of manufacturing the sensor element.

Description of the Related Art

Sensor elements made of ceramics are used for detecting the concentrations of gas components such as NOx and oxygen. Such sensor elements are used at high temperatures. There is a concern that the adhesion of water droplets to a body of the sensor element at high temperatures may cause the body to be damaged by thermal shocks.

JP 2016-109685 A discloses a sensor element that protects a main body from thermal shocks by covering the periphery of the main body with a porous protective layer.

JP 2009-080111 A also discloses a sensor element having a main body covered with a porous protective layer. The porous protective layer has concave portions on the surface thereof for capturing water droplets. The concave portions allow water droplets to dry quickly and prevent the porous protective layer from being damaged.

JP 2019-039693 A also discloses a sensor element having a main body covered with a porous protective layer. JP 2019-039693 A discloses the porous protective layer in which the film thickness of the corner portions vulnerable to water droplets is increased in order to prevent damage to the porous protective layer by water droplets.

SUMMARY OF THE INVENTION

However, in each of the sensor elements disclosed in JP 2016-109685 A, JP 2009-080111 A, and JP 2019-039693 A, a tip portion of the main body, which is the weakest portion, cannot be efficiently protected, and therefore, it is necessary to make the porous protective layer thick as a whole. The thick porous protective layer takes time to produce, and causes problems such as an increase in power consumption at the time of starting due to an increase in heat capacity and a deterioration in the responsiveness of the sensor element due to an increase in gas diffusion time.

An object of the present invention is to solve the aforementioned problems.

Appendix 1

A sensor element according to one aspect of the present invention is provided with a main body including a cavity on a distal end side of the main body, the cavity being configured to take in a gas, and a porous protective layer covering an outer peripheral surface of the main body on the distal end side, wherein the porous protective layer includes a water droplet blocking structure covering at least a part of a distal end surface of the main body, the part overlapping with the cavity in a longitudinal direction perpendicular to the distal end surface, and a thin portion covering the distal end surface around the water droplet blocking structure. In the sensor element, the part of the distal end surface, which is the most susceptible to damage due to concentration of stress in the main body and overlaps the cavity in the longitudinal direction, is protected by the water droplet blocking structure, and the thin portion is provided around the part. Thus, the necessary part can be efficiently protected by the porous protective layer. As a result, the sensor element can reduce the thermal capacity of the distal end, and can improve the responsiveness of the sensor element.

Appendix 2

In the sensor element according to Appendix 1, the cavity may extend along the longitudinal direction, and the water droplet blocking structure may be a convex portion of the porous protective layer having a thickness larger than that of the thin portion. This sensor element can realize the water droplet blocking structure with the simplest possible structure.

Appendix 3

In the sensor element according to Appendix 1 or 2, the main body may be formed in a rectangular parallelepiped shape elongated in the longitudinal direction, and the main body may have a flat plate shape in which a dimension in a widthwise direction perpendicular to the longitudinal direction is larger than a dimension in a thickness direction perpendicular to the longitudinal direction and the widthwise direction, and the water droplet blocking structure may be positioned at a center of the distal end surface in the widthwise direction and the thickness direction.

Appendix 4

In the sensor element according to any one of Appendices 1 to 3, the thin portion may be formed at a position avoiding an extension line of the cavity in the longitudinal direction. The sensor element can prevent the main body from being damaged due to adhesion of water droplets.

Appendix 5

In the sensor element according to any one of Appendices 1 to 4, a ratio B/A of a difference value B between a thickness C of the thin portion and a thickness A of the water droplet blocking structure, to the thickness A of the water droplet blocking structure, may be in a range of 0.05 to 0.6. The sensor element can achieve both productivity of the porous protective layer and resistance to damage of the main body due to adhesion of water droplets.

Appendix 6

In the sensor element according to any one of Appendices 1 to 4, a ratio B/A of a difference value B between a thickness C of the thin portion and a thickness A of the water droplet blocking structure, to the thickness A of the water droplet blocking structure, may be in a range of 0.1 to 0.58. This sensor element is more suitable in terms of productivity and resistance to damage of the main body due to adhesion of water droplets.

Appendix 7

In the sensor element according to any one of Appendices 1 to 6, the cavity may open on the distal end surface.

Appendix 8

Another aspect of the present invention is a method of manufacturing a sensor element provided with a main body including a cavity on a distal end side of the main body, the cavity configured to take in a gas, and a porous protective layer covering an outer peripheral surface of the main body on the distal end side, and the method includes depositing the porous protective layer on a side surface of the main body by plasma spraying, as a first thermal spraying process, and depositing the porous protective layer on a distal end surface of the main body by the plasma spraying, as a second thermal spraying process, wherein the second thermal spraying process includes arranging a thermal spraying gun so as to face the distal end surface and aligning a nozzle center, at which a deposition efficiency of the thermal spraying gun is highest, on an extension line of the cavity in a longitudinal direction perpendicular to the distal end surface, performing plasma thermal spraying, and thereby forming the porous protective layer including a thick convex portion covering at least a part of the distal end surface, the part overlapping the cavity in the longitudinal direction, and a thin portion covering the distal end surface around the convex portion. In the above method of manufacturing the sensor element, since it is not necessary to move the nozzle center of the thermal spraying gun greatly in the second thermal spraying process, the porous protective layer can be manufactured more efficiently.

Appendix 9

Still another aspect of the present invention is a method of manufacturing a sensor element provided with a main body including a cavity on a distal end side of the main body, the cavity configured to take in a gas, and a porous protective layer covering an outer peripheral surface of the main body on the distal end side, and the method includes depositing the porous protective layer on a side surface of the main body by cold spraying, as a first spraying process, and depositing the porous protective layer on a distal end surface of the main body by the cold spraying, as a second spraying process, wherein the second spraying process includes arranging a spraying gun so as to face the distal end surface and aligning a nozzle center, at which a deposition efficiency of the spraying gun is highest, on an extension line of the cavity in a longitudinal direction perpendicular to the distal end surface, performing spraying, and thereby forming the porous protective layer including a thick convex portion covering at least a part of the distal end surface, the part overlapping the cavity in the longitudinal direction, and a thin portion covering the distal end surface around the convex portion. In the above method of manufacturing the sensor element, since it is not necessary to move the nozzle center of the spray gun greatly in the second spraying process, the porous protective layer can be manufactured more efficiently.

The sensor element and the method of manufacturing the sensor element as described above can reduce the thickness of the porous protective layer while protecting the main body from thermal shocks.

The above and other objects, features, and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIG. 8 is a table showing positions of thin portions of the sensor elements, thicknesses A of convex portions, difference values B in thickness between thin portions and the convex portions, ratios B/A between the difference values and the thicknesses of the convex portions, evaluation results of water resistance, and evaluation results of productivity, according to Comparative Examples 1 to 3 and Exemplary Embodiments 1 to 5.

DETAILED DESCRIPTION OF THE INVENTION

Figure 1:
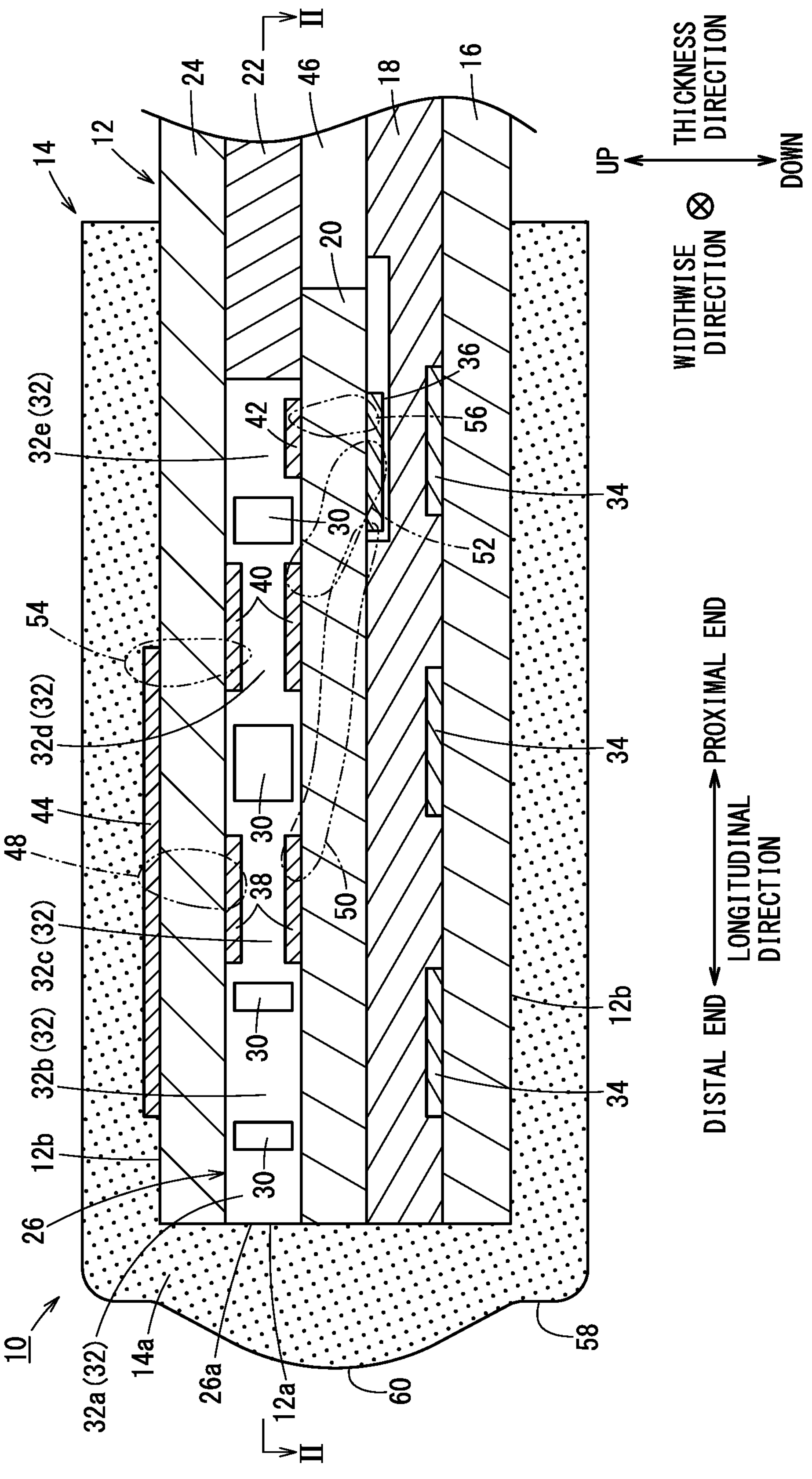
FIG. 1 is a longitudinal sectional view of a sensor element according to an embodiment.

A sensor element 10 according to the present embodiment shown in FIG. 1 is used for a gas sensor for detecting the concentrations of gas components such as NOx in automotive exhaust gas. The sensor element 10 has a main body 12 and a porous protective layer 14. The main body 12 has a long rectangular parallelepiped shape and extends long in a longitudinal direction which is a left-right direction in the drawing. The main body 12 has a thickness direction in an up-down direction in the drawing, and a widthwise direction in the direction perpendicular to the sheet surface of the drawing. The main body 12 has a flat plate shape in which the dimension in the thickness direction is smaller than the dimension in the widthwise direction. The porous protective layer 14 covers an outer surface near a distal end of the main body 12, thereby protecting the main body 12 from thermal shocks.

The main body 12 has a structure in which a plurality of ceramic layers having oxygen ion conductivity, made of zirconia ($ZrO_2$) or the like, are stacked. Specifically, the main body 12 has a first layer 16, a second layer 18, a third layer 20, a fourth layer 22, and a fifth layer 24 in order from the bottom of the drawing. The layers are bonded together and integrated. Wiring patterns are provided at predetermined positions between the respective layers. The first layer 16 and the second layer 18 of the main body 12 may be made of an insulating material such as alumina.

The fourth layer 22 is provided with a cavity 26. The cavity 26 is a hollow portion formed in the main body 12 for taking in gas components to be measured and performing measurement. The cavity 26 is formed near the distal end of the main body 12 (on the left side in the drawing). The cavity 26 extends in the longitudinal direction. The cavity 26 introduces a gas to be measured into the inside of the main body 12 from an opening 26*a*. In the illustrated example, the opening 26*a* is located on a distal end surface 12*a* of the main body 12. The position of the opening 26*a* of the cavity 26 is not necessarily limited to the distal end surface 12*a* of the main body 12, and may be formed in a portion other than the distal end surface 12*a*, such as a side surface 12*b* in the widthwise direction of the main body 12. The opening 26*a* of the cavity 26 is not limited to the hollow portion, and may be a gas introduction port of porous material, for example.

The cavity 26 is partitioned by a plurality of diffusion rate control members 30. The cavity 26 partitioned by the diffusion rate control members 30 constitutes a plurality of vacant chambers 32. The vacant chamber 32 on the distal end side at the forefront is a gas introduction part 32*a*, and the second vacant chamber 32 from the distal end side is a buffer space 32*b*. The third vacant chamber 32 from the distal end side is a first vacant chamber 32*c*, the fourth vacant chamber 32 from the distal end side is a second vacant chamber 32*d*, and the fifth vacant chamber 32 from the distal end side is a third vacant chamber 32*e*. The first vacant chamber 32*c* is a vacant chamber 32 in which the oxygen concentration of the gas components flowing therein is adjusted. The second vacant chamber 32*d* is a vacant chamber 32 for further reducing oxygen from the gas components to be measured. The third vacant chamber 32*e* is a vacant chamber 32 for measuring gas components to be measured.

A part of the wiring pattern of the main body 12 constitutes a heater 34, a reference electrode 36, a main pump electrode 38, an auxiliary pump electrode 40, a measurement electrode 42, and an outer side electrode 44. The heater 34 is located between the first layer 16 and the second layer 18. The heater 34 generates heat due to supply of current and heats the sensor element 10 to a predetermined operating temperature.

The reference electrode 36 is located between the second layer 18 and the third layer 20. The reference electrode 36 is in contact with the third layer 20 and is in contact with a reference gas (e.g., atmosphere air) through a reference gas introduction part 46.

The main pump electrode 38 is provided on an inner peripheral surface of the first vacant chamber 32*c*. The auxiliary pump electrode 40 is provided on an inner peripheral surface of the second vacant chamber 32*d*. The measurement electrode 42 is located in the third vacant chamber 32*e* and is provided on the third layer 20. The outer side electrode 44 is provided on an outer surface of the fifth layer 24. The description of the other electrodes and wirings of the main body 12 is omitted.

An oxygen partial pressure in the first vacant chamber 32*c* is detected by the first oxygen detecting cell 50. The first oxygen detecting cell 50 is an electrochemical cell comprising the main pump electrode 38, the third layer 20, and the reference electrode 36. The first oxygen detecting cell 50 generates a potential difference between the main pump electrode 38 and the reference electrode 36 in accordance with the oxygen partial pressure in the first vacant chamber 32*c*. The oxygen in the first vacant chamber 32*c* is regulated by the main pump cell 48. The main pump cell 48 is an electrochemical cell comprising the main pump electrode 38, the fifth layer 24, and the outer side electrode 44. The main pump cell 48 introduces oxygen into the first vacant chamber 32*c* or discharges oxygen from the first vacant chamber 32*c* through the fifth layer 24. The main pump cell 48 regulates the oxygen partial pressure in the first vacant chamber 32*c* to a predetermined value.

The oxygen partial pressure in the second vacant chamber 32*d* is detected by a second oxygen detecting cell 52. The second oxygen detecting cell 52 is constituted by the auxiliary pump electrode 40, the third layer 20, and the reference electrode 36. The detected value of the second oxygen detecting cell 52 is used for controlling an auxiliary pump cell 54. The auxiliary pump cell 54 is constituted by the auxiliary pump electrode 40, the fifth layer 24, and the outer side electrode 44. The auxiliary pump cell 54 discharges oxygen from the inside of the second vacant chamber 32*d* to reduce the oxygen concentration of the gas therein.

The concentration of the gas to be measured (e.g., NO) in the third vacant chamber 32*e* is detected by a measurement pump cell 56. The measurement pump cell 56 is constituted by the measurement electrode 42, the third layer 20, and the reference electrode 36.

The porous protective layer 14 covers the outer peripheral surface of the main body 12 at the distal end side. Specifically, the porous protective layer 14 covers the distal end surface 12*a* located at the distal end of the main body 12 and the four side surfaces 12*b* adjacent to the distal end surface 12*a*. The porous protective layer 14 is made of a porous material. The porous protective layer 14 has a structure in which ceramic particles are bonded to each other while forming pores. Examples of the material of the porous protective layer 14 include alumina, zirconia, spinel, cordierite, titania, and magnesia. The porosity of the porous protective layer 14 is, for example, 5% by volume to 40% by volume. The porous protective layer 14 may have a multilayer structure having an inner layer 66 (FIG. 7) and an outer layer 68 (FIG. 7) having different porosities. In the porous protective layer 14 having a multilayer structure, the inner layer 66 preferably has a larger porosity.

The porous protective layer 14 of the present embodiment has a thin portion 58 and a convex portion 60 (water droplet blocking structure) at a distal end portion 14*a* covering the distal end surface 12*a*. The thin portion 58 is a portion having a relatively small thickness at the distal end portion 14*a* of the porous protective layer 14 covering the distal end surface 12*a*. The thin portion 58 reduces the amount of the porous protective layer 14, thereby reducing the heat capacity of the porous protective layer 14. Also, the thin portion 58 shortens diffusion paths of the porous protective layer 14 required for the gas to be measured to reach the opening 26*a* of the cavity 26. Therefore, the thin portion 58 can make the gas to be measured reach the cavity 26 more quickly, and can increase a response speed of the sensor element 10.

Figure 2:
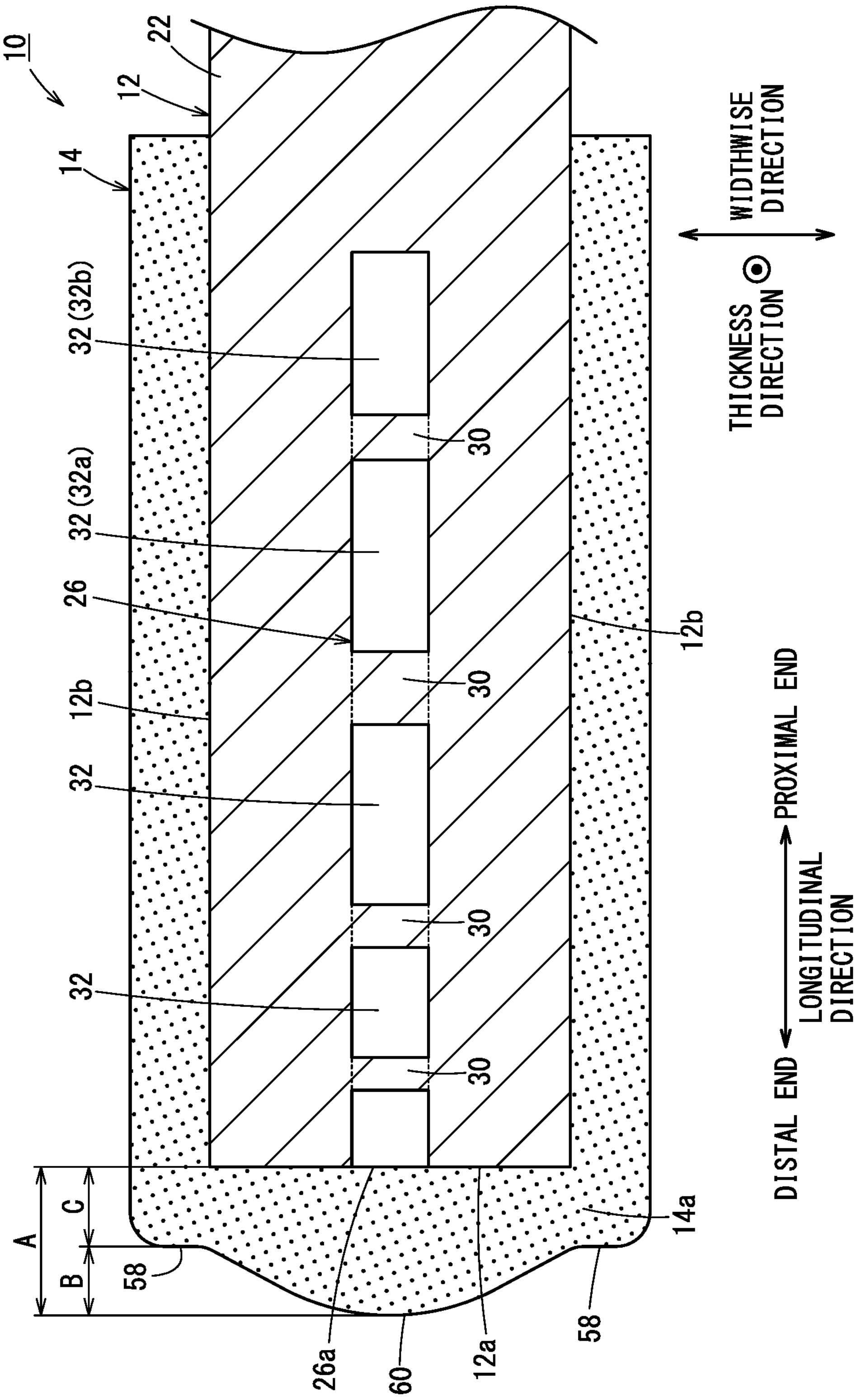
FIG. 2 is a cross-sectional view taken along line II-II of FIG. 1.

The thin portion 58 has a lower performance than the convex portion 60 in protecting the main body 12 from water droplets. Therefore, the thin portion 58 is formed at a position avoiding the extension line or area of the cavity 26 in the longitudinal direction. That is, the thin portion 58 is formed at a portion in the main body 12 where cracks are relatively unlikely to occur. That is, the thin portion 58 is formed at a position outside the range surrounded by the extension line of the cavity 26 in the longitudinal direction. As shown in FIGS. 1 and 2, the thin portion 58 is formed near the peripheral edge portion of the distal end surface 12*a*.

The convex portion 60 is a part of the distal end portion 14*a* formed to have a relatively large thickness, and projects in a convex shape from the thin portion 58 toward the distal end. As shown in FIGS. 1 and 2, the convex portion 60 is located at the center in the thickness direction and at the center in the widthwise direction, of the main body 12. The convex portion 60 is thicker than the thin portion 58, and therefore prevents water droplets adhering to the surface from reaching the main body 12. That is, the convex portion 60 constitutes the water droplet blocking structure of the present embodiment.

Particularly, in the portion of the distal end surface 12*a* of the main body 12 where the cavity 26 is extended in the longitudinal direction, stress is likely to concentrate thereon. Thus, the portion is likely to be broken by thermal shocks. Even when the opening 26*a* of the cavity 26 is formed in any of the side surfaces 12*b* of the main body 12, similarly, the part of the distal end surface 12*a* on an extension line of the cavity 26 in the longitudinal direction is easily cracked due to concentration of stress. Therefore, in the present embodiment, the convex portion 60 is provided so as to cover the part of the distal end surface 12*a*, which is a part on the extension line of the cavity 26 in the longitudinal direction and is easily damaged by thermal shocks. As shown in FIGS. 1 and 2, in the present embodiment, the convex portion 60 is positioned at a substantially center in the widthwise direction and the thickness direction, so as to cover the part of the distal end surface 12*a* on the extension line of the cavity 26 in the longitudinal direction.

A thickness A of the convex portion 60 may be, for example, 300 μm or more. A difference value B in thickness between the thin portion 58 and the convex portion 60 may be, for example, 5 to 60%, more preferably 10 to 58% of the thickness A of the convex portion 60. That is, a ratio B/A of the difference value B to the thickness A is preferably in the range of 0.05 to 0.6, more preferably in the range of 0.1 to 0.58. A thickness C of the thin portion 58 can be set to 40 to 95% of the thickness A of the convex portion 60.

The sensor element 10 of the present embodiment is configured as described above. The sensor element 10 is manufactured by the following method.

First, the main body 12 is manufactured. The main body 12 is produced by stacking and firing a plurality of green sheets. A method of manufacturing the main body 12 is described in, for example, JP 2008-164411 A or JP 2009-175099 A.

Figure 3A:
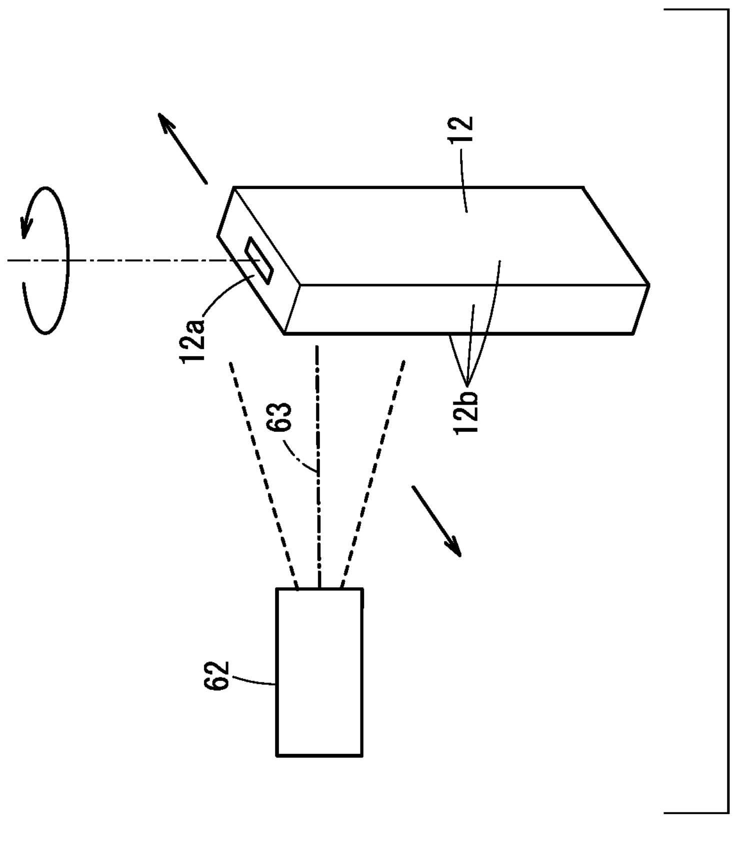
FIG. 3A is an explanatory diagram of a first thermal spraying process.

Next, the porous protective layer 14 is formed on the surface of the main body 12. The porous protective layer 14 is formed by plasma spraying. The step of forming the porous protective layer 14 includes a first thermal spraying process shown in FIG. 3A and a second thermal spraying process shown in FIG. 3B. As shown in FIG. 3A, the first thermal spraying process is a step of forming the porous protective layers 14 on the four side surfaces 12*b* of the main body 12.

In the first thermal spraying process, a raw material powder such as alumina powder is thermally sprayed from a plasma spraying gun 62 disposed to face the side surface 12*b* of the main body 12. The plasma spraying gun 62 is positioned such that its nozzle center line 63 is perpendicular to the side surfaces 12*b*. The nozzle center line 63 is the central axis of a jet flow of the plasma spraying gun 62, and most of the raw material powder is sprayed in the center line. In the first spraying process, the main body 12 is rotated about its longitudinal axis in order to form the porous protective layer 14 of uniform thickness on the four side surfaces 12*b*. In the first thermal spraying process, the main body 12 reciprocates in front of the plasma spraying gun 62 a plurality of times.

Figure 3B:
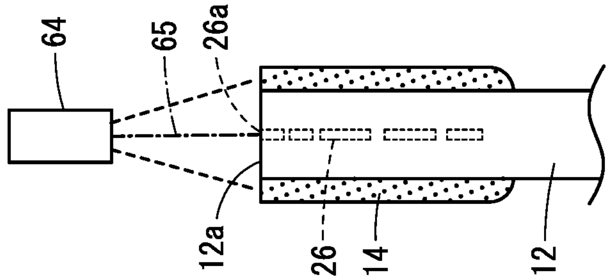
FIG. 3B is an explanatory diagram of a second thermal spraying process.

Next, as shown in FIG. 3B, a second thermal spraying process is performed. In the second thermal spraying process, raw material powder such as alumina powder is thermally sprayed from a plasma spraying gun 64 disposed to face the distal end surface 12*a* of the main body 12. The plasma spraying gun 64 is disposed such that a nozzle center line 65 thereof faces the longitudinal direction of the main body 12. Further, the plasma spraying gun 64 is positioned such that the nozzle center line 65 coincides with the longitudinal extension line of the cavity 26.

The nozzle center line 65 is positioned at a center position of the jet flow of the plasma spraying gun 64, and the density of the raw material powder is highest. The nozzle center line 65 is a portion where the porous protective layer 14 is deposited at fastest rate and the film forming efficiency is highest. As the distance from the nozzle center line 65 increases, the density of the raw material powder decreases, and the deposition rate (deposition efficiency) of the porous protective layer 14 decreases. Therefore, when the nozzle center line 65 is positioned on the extension line of the cavity 26 in the longitudinal direction (the opening 26*a* in the present embodiment) and the spray is applied, the convex portion 60 is formed so as to cover the part overlapping the cavity 26 in the longitudinal direction. In the present embodiment, since the cavity 26 is positioned at the approximate center in the widthwise direction and the thickness direction of the main body 12, the nozzle center line 65 is positioned at the approximate center in the widthwise direction and the thickness direction of the main body 12. The thin portion 58 is formed at the peripheral edge portion of the convex portion 60. The plasma spraying gun 64 may be moved relative to the main body 12 within a range in which the nozzle center line 65 does not largely deviate from the opening 26*a* of the cavity 26.

Conventionally, in order to make the porous protective layer 14 have a uniform thickness, it is necessary to move the plasma spraying gun 64 or the main body 12, i.e., to move the portion where a high deposition efficiency of the plasma spraying gun is obtained so as to uniform the deposition thickness, and the productivity is lowered. In contrast, in the second thermal spraying process, since the plasma spraying gun 64 does not need to be moved and the deposition thickness need not necessarily be uniform, the porous protective layer 14 can be formed more efficiently, and the plasma spraying is completed in a shorter time. Thus, the productivity is also improved.

The sensor element 10 of the present embodiment is completed by the above processes.

The method of manufacturing the sensor element 10 according to the present embodiment may be a cold spray method (cold spraying) instead of the plasma spraying. In this case, spray guns are used instead of the plasma spraying guns 62 and 64. In this case, the method may include a first spraying process of forming the porous protective layer 14 on the side surfaces 12*b* of the main body 12 and a second spraying process of forming the porous protective layer 14 on the distal end surface 12*a* of the main body 12. In the second spraying step, the center line of the spray gun is positioned in the opening 26*a* of the cavity 26. As a result, the porous protective layer 14 having the convex portion 60 on the extension line of the cavity 26 in the longitudinal direction is formed.

Hereinafter, examples, in each of which the sensor element 10 was manufactured, will be described as Exemplary Embodiments and Comparative Examples.

Comparative Example 1

Figure 4:
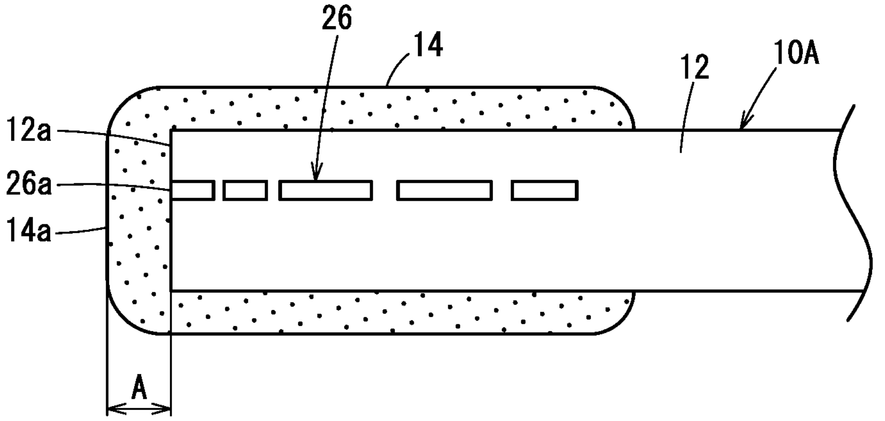
FIG. 4 is a schematic cross-sectional view of a sensor element according to Comparative Example 1.

As shown in FIG. 4, a sensor element 10A according to Comparative Example 1 had a porous protective layer 14 formed by a conventional method (shown in JP 2016-109685 A). A porous protective layer 14 of Comparative Example 1 was formed to have a uniform thickness at a distal end portion 14*a*, and did not have any portions corresponding to the thin portion 58 and the convex portion 60. The thickness A of the porous protective layer 14 of Comparative Example 1 at the distal end portion 14*a* was 500 μm.

Comparative Examples 2 and 3

Figure 5B:
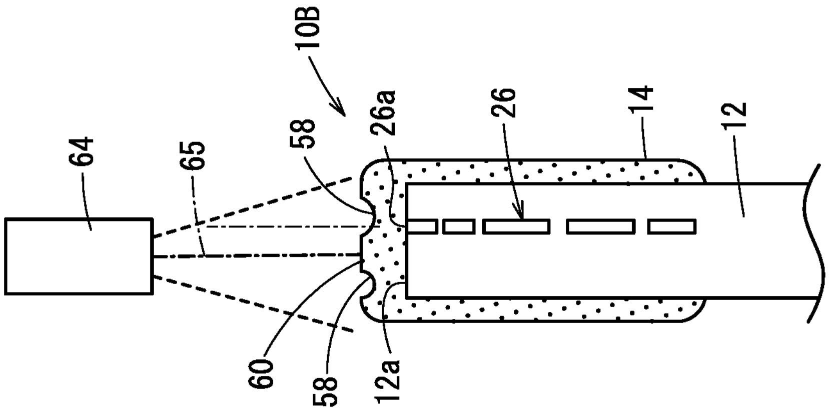
FIG. 5B is an explanatory diagram of a second thermal spraying process according to Comparative Examples 2 and 3.
Figure 5A:
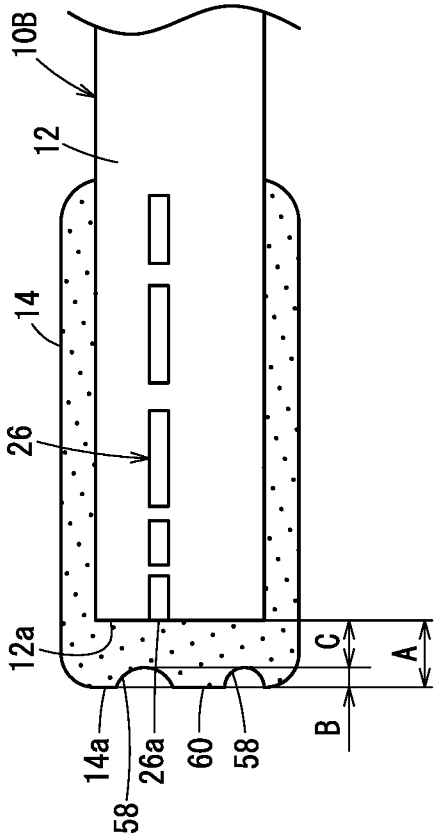
FIG. 5A is a schematic cross-sectional view of a sensor element according to Comparative Examples 2 and 3.

As shown in FIG. 5A, a sensor element 10B according to Comparative Example 2 had a thin portion 58 and a convex portion 60 at a distal end portion 14*a* of a porous protective layer 14. In the porous protective layer 14 of Comparative Examples 2 and 3, however, the part (opening 26*a*) on the extension line of a cavity 26 in the longitudinal direction was not covered with the convex portion 60 but covered with the thin portion 58. The porous protective layer 14 was produced by positioning the nozzle center line 65 of the plasma spraying gun 64 at a position different from the position on the extension line of the cavity 26, in the second thermal spraying process shown in FIG. 5B.

In the porous protective layer 14 of Comparative Example 2, the thickness A of the convex portion 60 was 530 μm. In Comparative Example 2, the difference value B in thickness between the thin portion 58 and the convex portion 60 was 130 μm.

The sensor element 10B according to Comparative Example 3 had the same structure as that of FIG. 5A. In the sensor element 10B of Comparative Example 3, the thickness A of the convex portion 60 was 500 μm, and the difference value B in thickness between the thin portion 58 and the convex portion 60 was 320 μm.

Exemplary Embodiments 1 and 2

Figure 6A:
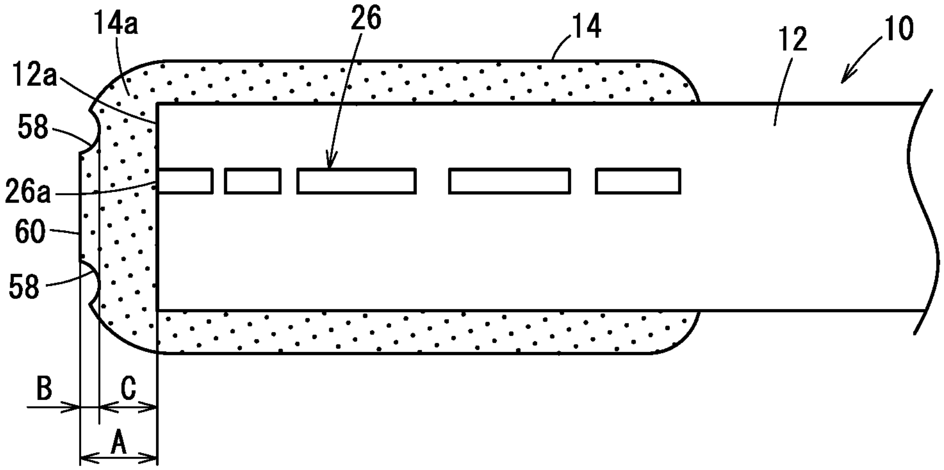
FIG. 6A is a schematic cross-sectional view of a sensor element according to Exemplary Embodiment 1.

As shown in FIG. 6A, the sensor element 10 according to Exemplary Embodiment 1 had the thin portion 58 and the convex portion 60 at the distal end portion 14*a* of the porous protective layer 14. The convex portion 60 covered the part (opening 26*a*) on the extension line of the cavity 26 in the longitudinal direction, and the thin portion 58 was provided at the position avoiding the extension line of the cavity 26 in the longitudinal direction. In Exemplary Embodiment 1, the thickness A of the convex portion 60 was 500 μm, and the difference value B in thickness between the thin portion 58 and the convex portion 60 was 50 μm.

Figure 6B:
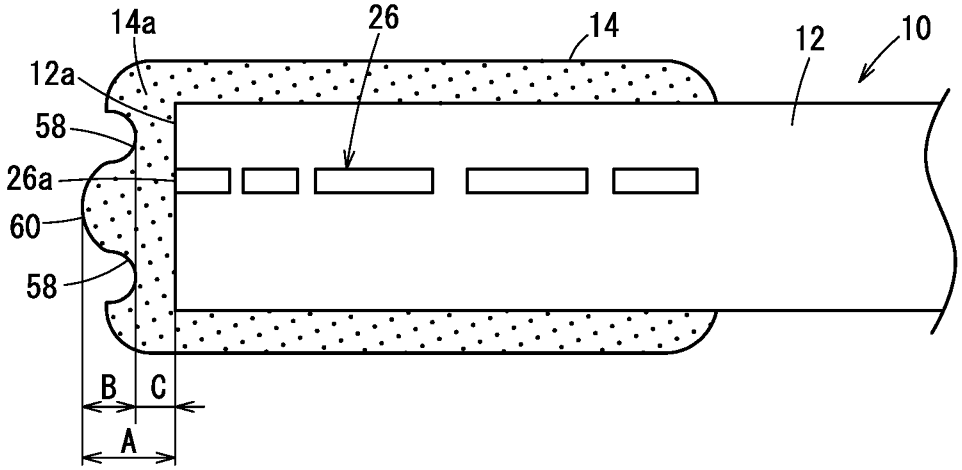
FIG. 6B is a schematic cross-sectional view of a sensor element according to Exemplary Embodiment 2.

As shown in FIG. 6B, the sensor element 10 according to Exemplary Embodiment 2 had the thin portion 58 and the convex portion 60 at the distal end portion 14*a* of the porous protective layer 14. The convex portion 60 covered the part (opening 26*a*) on the extension line of the cavity 26 in the longitudinal direction, and the thin portion 58 was provided at the position avoiding a part on the extension line of the cavity 26 in the longitudinal direction. In Exemplary Embodiment 2, the thickness A of the convex portion 60 was 480 μm, and the difference value B in thickness between the thin portion 58 and the convex portion 60 was 280 μm.

Exemplary Embodiment 3

Figure 7:
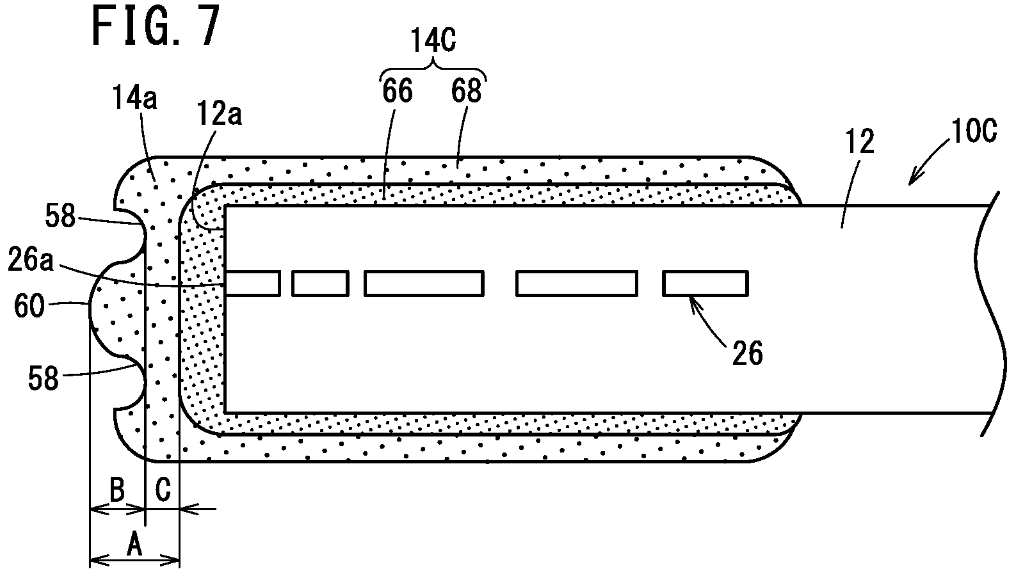
FIG. 7 is a schematic cross-sectional view of a sensor element according to Exemplary Embodiment 3.

As shown in FIG. 7, a sensor element 10C according to Exemplary Embodiment 3 had a porous protective layer 14C having a two-layer structure. The porous protective layer 14C had an inner layer 66 having a large porosity and in contact with the main body 12, and an outer layer 68 formed on the inner layer 66 and having a smaller porosity than that of the inner layer 66. The inner layer 66 was formed to have a uniform thickness by, for example, plasma spraying or dipping. The outer layer 68 was formed in the first thermal spraying process (FIG. 3A) and the second thermal spraying process (FIG. 3B). The outer layer 68 had the convex portion 60 positioned on a part on the extension line of the cavity 26 in the longitudinal direction and a thin portion 58 covering a part other than the extension line of the cavity 26 in the longitudinal direction. The thickness A of the convex portion 60 of the sensor element 10C of Exemplary Embodiment 3 was 900 μm, and the difference value B in thickness between the thin portion 58 and the convex portion 60 was 300 μm.

Exemplary Embodiment 4

The sensor element 10 according to Exemplary Embodiment 4 had a porous protective layer 14 having a cross-sectional shape substantially similar to that shown in FIG. 6B. In Exemplary Embodiment 4, the thickness A of the convex portion 60 was 500 μm, and the difference value B in thickness between the thin portion 58 and the convex portion 60 was 300 μm.

Exemplary Embodiment 5

The sensor element 10 according to Exemplary Embodiment 5 had a porous protective layer 14 having a cross-sectional shape substantially similar to the cross-sectional shape shown in FIG. 6A. In Exemplary Embodiment 5, the thickness A of the convex portion 60 was 600 μm, and the difference value B in thickness between the thin portion 58 and the convex portion 60 was 30 μm.

Method of Evaluating Water Resistance

With respect to the sensor elements 10 to 10C of Comparative Examples 1 to 3 and Exemplary Embodiments 1 to 5, the evaluation was performed as to the water resistance of the porous protective layers 14 and 14C, and the productivity. The evaluation of the water resistance was carried out as follows.

First, the main body 12 was heated to a temperature of 800° C. by the energization of the heater 34. In this state, the main pump cell 48, the auxiliary pump cell 54, the first oxygen detecting cell 50, the second oxygen detecting cell 52, and the like were operated under air atmosphere. The main pump cell 48 was controlled such that the oxygen concentration in the first vacant chamber 32*c* was maintained at a predetermined constant value. The current supplied to the main pump cell 48 to maintain the oxygen concentration at a constant value was detected as a pump current Ip0. After waiting for stabilization of the pump current Ip0 of the main pump cell 48, an operation of dripping water droplets onto the porous protective layers 14 and 14C was performed.

Thereafter, the presence or absence of cracks in the main body 12 is determined based on whether or not the pump current Ip0 has changed to a value exceeding a predetermined threshold value. When the main body 12 is cracked by thermal shocks due to water droplets, oxygen easily flows into the first vacant chamber 32*c* through the cracked portion, and therefore the value of the pump current Ip0 increases. Therefore, when the pump current Ip0 exceeds a predetermined threshold value, it is determined that the main body 12 has been cracked due to the water droplets. When the amount of supplied water droplets causing cracking of the main body 12 was less than 7 μL, it was determined to be poor (x). When the amount of supplied water droplets causing cracking was 7 μL or more, it was determined to be fair (triangle). When the amount of supplied water droplets causing cracking was 10 μL or more, it was determined to be good (circle). When the amount of supplied water droplets causing cracking was 20 μL or more, it was determined to be excellent (double circle).

Method of Evaluating Productivity

The productivity was evaluated by the film formation rate (second thermal spraying process) of the distal end portion 14*a* of the porous protective layer 14. The deposition rate of Comparative Example 1 was selected as the reference value. When the deposition rate by plasma spraying was equal to or lower than the deposition rate of Comparative Example 1, it was determined to be poor (x). When the deposition rate was 5% or more faster than the deposition rate of Comparative Example 1, it was determined to be fair (triangle). When the deposition rate was 20% or more faster than the deposition rate of Comparative Example 1, it was determined to be good (circle). Further, when the deposition rate was 30% or more faster than the deposition rate of Comparative Example 1, it was determined to be excellent (double circle).

Evaluation Results

FIG. 8 collectively shows items concerning whether the thin portion 58 is located on an extension line of the cavity 26 in the longitudinal direction, the thickness A of the convex portion 60, the difference value B in thickness between the thin portion 58 and the convex portion 60, the ratio B/A of the difference value B to the thickness A, the evaluation result of the water resistance, and the evaluation result of the productivity, for each of Comparative Examples 1 to 3 and Exemplary Embodiments 1 to 5.

As shown in FIG. 8, from the results of Comparative Examples 1 to 3 and Exemplary Embodiments 1 to 5, it has been confirmed that the deposition rate (productivity) is improved by providing the thin portion 58 and the convex portion 60 in the porous protective layer 14 in the case of performing the plasma spraying. From the viewpoint of productivity, the value of the ratio B/A is preferably 0.05 or more in the sensor elements 10 to 10C. When the ratio B/A is 0.1 or more, the deposition rate is 20% or more faster than that of Comparative Example 1, and higher productivity is obtained.

Further, as shown in Comparative Examples 2 and 3, when the thin portion 58 was disposed on an extension line of the cavity 26 in the longitudinal direction, sufficient water resistance was not obtained. In order to secure the water resistance, it has been confirmed that the thin portion 58 should be provided at a position avoiding the extension line of the cavity 26 in the longitudinal direction, as shown in Exemplary Embodiments 1 to 5.

From the results of Exemplary Embodiments 1 to 5, when the ratio B/A was in the range of 0.05 to 0.6, it has been determined to be fair (triangle) or better, as to the water resistance. When the ratio B/A is 0.58 or less, the water resistance is good (circle) or excellent (double circle), and higher water resistance is obtained.

From the results of Exemplary Embodiments 1 to 5, it has been confirmed that the water resistance and the productivity can be compatible when the ratio B/A of the difference value B in thickness between the thin portion 58 and the convex portion 60 to the thickness A of the convex portion 60 is at least in the range of 0.05 to 0.6. Further, the results show that when the ratio B/A is in the range of 0.1 to 0.58, more preferable water resistance and productivity are obtained.

The present invention is not limited to the above-described embodiments, and various configurations can be adopted therein without departing from the essence and gist of the present invention. That is, the water droplet blocking structure is not limited to the convex portion 60, and may be a dense portion (a portion having a porosity lower than that of the thin portion 58 or a portion having a porosity of approximately 0%) that makes it difficult for water droplets to enter. In this case, the thickness A of the water droplet blocking structure may be equal to or smaller than the thickness C of the thin portion 58.

The invention claimed is:

1. A sensor element comprising:

a main body including a cavity on a distal end side of the main body, the cavity being configured to take in a gas; and a porous protective layer covering an outer peripheral surface of the main body on the distal end side, wherein the porous protective layer comprises:

a water droplet blocking structure covering at least a part of a distal end surface of the main body, the part overlapping with the cavity in a longitudinal direction perpendicular to the distal end surface; and a thin portion that is thinner than the water droplet blocking structure and covering the distal end surface around the water droplet blocking structure and having an outer surface that is parallel to the distal end surface, and wherein the thin portion shortens diffusion paths required for the gas to reach an opening of the cavity.

2. The sensor element according to claim 1, wherein the cavity extends along the longitudinal direction, and the water droplet blocking structure is a convex portion of the porous protective layer having a thickness larger than that of the thin portion.

3. The sensor element according to claim 1, wherein the main body is formed in a rectangular parallelepiped shape elongated in the longitudinal direction, and the main body has a flat plate shape in which a dimension in a widthwise direction perpendicular to the longitudinal direction is larger than a dimension in a thickness direction perpendicular to the longitudinal direction and the widthwise direction, and the water droplet blocking structure is positioned at a center of the distal end surface in the widthwise direction and the thickness direction.

4. The sensor element according to claim 1, wherein the thin portion is formed at a position avoiding an extension line of the cavity in the longitudinal direction.

5. The sensor element according to claim 1, wherein a ratio B/A of a difference value B between a thickness C of the thin portion and a thickness A of the water droplet blocking structure, to the thickness A of the water droplet blocking structure, is in a range of 0.05 to 0.6.

6. The sensor element according to claim 1, wherein a ratio B/A of a difference value B between a thickness C of the thin portion and a thickness A of the water droplet blocking structure, to the thickness A of the water droplet blocking structure, is in a range of 0.1 to 0.58.

7. The sensor element according to claim 1, wherein the cavity opens on the distal end surface.

8. A method of manufacturing a sensor element provided with a main body including a cavity on a distal end side of the main body, the cavity configured to take in a gas, and a porous protective layer covering an outer peripheral surface of the main body on the distal end side, the method comprising:

depositing the porous protective layer on a side surface of the main body by plasma spraying, as a first thermal spraying process; and depositing the porous protective layer on a distal end surface of the main body by the plasma spraying, as a second thermal spraying process, wherein the second thermal spraying process comprises arranging a thermal spraying gun so as to face the distal end surface and aligning a nozzle center, at which a deposition efficiency of the thermal spraying gun is highest, on an extension line of the cavity in a longitudinal direction perpendicular to the distal end surface, performing plasma thermal spraying, and thereby forming the porous protective layer including a convex portion covering at least a part of the distal end surface, the part overlapping the cavity in the longitudinal direction, and a thin portion that is thinner than the convex portion and covering the distal end surface around the convex portion and having an outer surface that is parallel to the distal end surface, and wherein the thin portion shortens diffusion paths required for the gas to reach an opening of the cavity.

9. A method of manufacturing a sensor element provided with a main body including a cavity on a distal end side of the main body, the cavity configured to take in a gas, and a porous protective layer covering an outer peripheral surface of the main body on the distal end side, the method comprising:

depositing the porous protective layer on a side surface of the main body by cold spraying, as a first spraying process; and depositing the porous protective layer on the distal end surface of the main body by the cold spraying, as a second spraying process, wherein the second spraying process comprises arranging a spraying gun so as to face the distal end surface and aligning a nozzle center, at which a deposition efficiency of the spraying gun is highest, on an extension line of the cavity in a longitudinal direction perpendicular to the distal end surface, performing spraying, and thereby forming the porous protective layer including a convex portion covering at least a part of the distal end surface, the part overlapping the cavity in the longitudinal direction, and a thin portion that is thinner than the convex portion and covering the distal end surface around the convex portion and having an outer surface that is parallel to the distal end surface, and wherein the thin portion shortens diffusion paths required for the gas to reach an opening of the cavity.

10. A sensor element comprising:

a main body including a cavity at an end portion of the main body, the cavity being configured to take in a gas; and a porous protective layer provided on the main body and covering at least the end portion of the main body, wherein the porous protective layer comprises:

a water droplet blocking structure covering an area corresponding to the cavity; and a peripheral portion adjacent to the water droplet blocking structure and covering the end portion of the main body, wherein the peripheral portion includes a recessed portion formed at a position closer to a center of the main body than a peripheral edge of a distal end surface of the end portion of the main body, and wherein the porous protective layer is formed to have a thickness that is thinner at the recessed portion than at the peripheral edge of the distal end surface.

11. The sensor element according to claim 10, wherein the thin portion shortens diffusion paths required for the gas to reach an opening of the cavity.

* * * * *